United States Patent
Wu et al.

(10) Patent No.: US 8,962,305 B2
(45) Date of Patent: Feb. 24, 2015

(54) BIOSENSOR CHIP WITH NANOSTRUCTURES

(75) Inventors: Hung-Wei Wu, Tainan (TW); Yong-Han Hong, Kaohsiung (TW); Yu-Fu Chen, Tainan (TW); Yung-Wei Chen, Tainan (TW); Shu-Ting Teng, Tainan (TW)

(73) Assignee: Kun Shan University, Tainan (TW)

( * ) Notice: Subject to any disclaimer, the term of this patent is extended or adjusted under 35 U.S.C. 154(b) by 10 days.

(21) Appl. No.: 13/423,943

(22) Filed: Mar. 19, 2012

(65) Prior Publication Data

US 2013/0089919 A1    Apr. 11, 2013

(30) Foreign Application Priority Data

Oct. 5, 2011 (TW) .............................. 100136156 A

(51) Int. Cl.
*C12M 1/34* (2006.01)
*G01N 27/22* (2006.01)

(52) U.S. Cl.
CPC .............. *G01N 27/221* (2013.01); *C12M 1/34* (2013.01); *C12M 1/3407* (2013.01)
USPC .................. 435/287.1; 435/285.2; 435/283.1; 422/68.1; 422/82.01

(58) Field of Classification Search
CPC  C12M 1/34; C12M 1/3407; G01N 33/54366; G01N 33/54373; G01N 27/221; B01J 19/0046; B82Y 30/00
USPC .............. 435/287.1, 285.2, 283.1; 422/82.01, 422/68.1
See application file for complete search history.

(56) References Cited

U.S. PATENT DOCUMENTS

| | | | | |
|---|---|---|---|---|
| 4,110,715 A | * | 8/1978 | Reindel | 333/204 |
| 5,744,902 A | * | 4/1998 | Vig | 310/360 |
| 5,755,942 A | * | 5/1998 | Zanzucchi et al. | 422/68.1 |
| 7,682,567 B2 | * | 3/2010 | Itsuji et al. | 422/82.11 |
| 2002/0182627 A1 | * | 12/2002 | Wang et al. | 435/287.2 |
| 2005/0014201 A1 | * | 1/2005 | Deuthsch | 435/287.2 |
| 2006/0172279 A1 | * | 8/2006 | Smela et al. | 435/287.1 |
| 2009/0011946 A1 | * | 1/2009 | Majumdar et al. | 422/68.1 |
| 2010/0258443 A1 | * | 10/2010 | Fourkas et al. | 205/76 |
| 2011/0169511 A1 | * | 7/2011 | Nordin et al. | 324/692 |

FOREIGN PATENT DOCUMENTS

| TW | I333068 | 11/2010 |
|---|---|---|
| TW | 201114680 A1 | 5/2011 |
| WO | WO 2010/017635 | * 2/2010 |

OTHER PUBLICATIONS

Office Action of corresponding TW application, issued on Dec. 16, 2013.

* cited by examiner

*Primary Examiner* — Nathan Bowers
*Assistant Examiner* — Timothy Barlow
(74) *Attorney, Agent, or Firm* — CKC & Partners Co., Ltd.

(57) ABSTRACT

A biosensor chip with nano-structures. The biosensor chip includes a RF biosensor, comprising an isolated substrate; a ground plane; a filtering circuit; at least one cell detection area with nano-structures and a protection layer. The RF biosensor can detect the existence of the cancer cells, high frequency biological effects and the cells relationship between transfers by noninvasive method. The RF biosensor according to the invention can provide high accuracy and sensitivity in cancer cells detection.

7 Claims, 9 Drawing Sheets

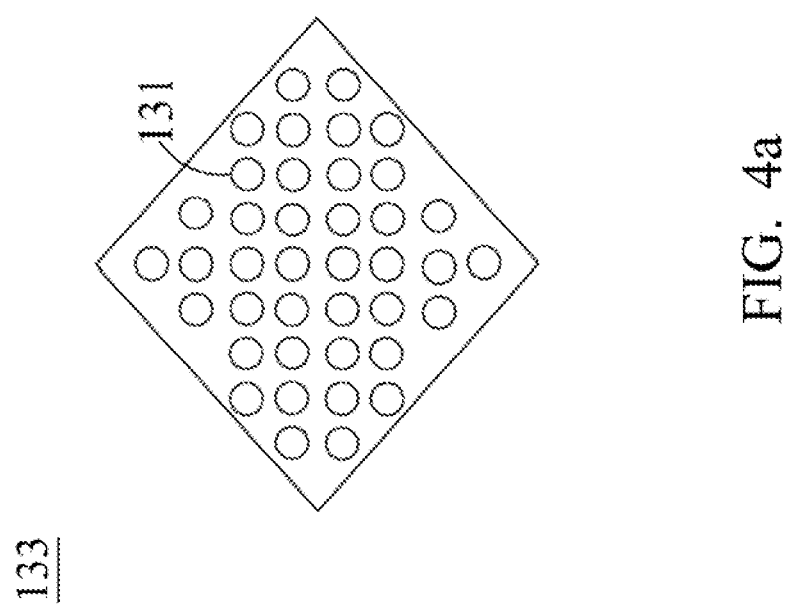

US 8,962,305 B2

BIOSENSOR CHIP WITH NANOSTRUCTURES

CROSS-REFERENCE TO RELATED APPLICATION

This application claims the benefit of Taiwan Patent Application No. 100136156, filed on Oct. 5, 2011, in the Taiwan Intellectual Property Office, the disclosure of which is incorporated herein in its entirety by reference.

BACKGROUND OF THE INVENTION

1. Field of the Invention

The present invention relates to a biosensor chip, and more particularly to a biosensor chip with nano-structures.

2. Description of the Related Art

According to current research and development, biosensor chips are usually divided into capillary electrophoresis chips and combination type chips. Two kinds of chips can provide a fast, accurate, high volume and automatic operating platform for sequencing analysis of deoxyribonucleic acid (DNA), screening of human's diseases, screening and development of new pharmaceuticals, medicine release and control, and food/environment inspection. For example, DNA detection chips have been widely applied in gene detection. Therefore, biosensor chips can complete a goal that is not achieved by conventional bio-detection. For instance, present cancer detection manner is usually detected when patients have certain symptoms or are on the danger lists. However, by utilizing technique of biosensor chips, doctors can be assisted to detect initially different kinds of cancers within a few minutes to further understand cancer genetic factors of patients so as to carry out prevention of the development of the disease. Technically, the chips produced by biomicro-electromachanical systems (BioMEMS) process have already shown promising development. However, BioMEMS have the shortcomings of high degree of difficulty in processing, high costs and short service life to be resolved.

Taking cancer cells as an example, when cancer cells within a body are increased to reach $10^7$ cells (about a tumor with a size of 0.2 centimeter), cancer cells carries out metastasis through angiogenesis of induced vessels. When cancer cells develop and reach a size of 1 centimeter, only then the cells can be observed by instruments (general physical examination). Unfortunately, the growth of cancer cells at this stage cannot be controlled completely, and the growing of cancer cells can be found by two manners of medical imaging and biochemical examinations in the early state.

During image examination, normal medical inspection includes X-ray photographs, ultrasonic or computer tomography that are difficult to find tumors with a size below 0.8 centimeter. Although tumors can be found by image examination, the found tumors are larger than 0.9 to 1.0 centimeter and may already have begun metastasis. Hence the foregoing tumors may not be effectively controlled or cured. During chemical examination, specificity combination between molecules is usually applied. For example, patients who have contracted acquired immune deficiency syndrome (AIDS) are usually inspected for the number of Helper T cells and Cytotoxin T Cells within the body. Both cells can be specifically expressed with two kinds of protein molecules CD4 and CD8. Therefore, a monoclonal antibody has affinity with CD4 or CD8 to accurately capture these cells. At this time, if the monoclonal antibody is labeled with fluorescent molecules, the number of Helper T cells and Cytotoxin T Cells can be determined according to intensity of fluorescent signals after measurement. Some cancers must reach certain sizes before the tumor label substance can be detected. Moreover, some cancers do not secrete tumor label substance, hence the existence of these cancer cells may not be sensitively screened with tumor labeling and at the same time, the kind of cancer cannot be confirmed. Thus, the sensitivity and specialty of the method need to be enhanced.

Another biochemical examination manner "DR-70" is different from a normal tumor label. Its principle is to detect substances produced within the human body when reacting with cancer cells. When cancer cells start entering intercellular matrix from cancer in situ, human connective tissues would produce fibrinogen degradation products (FDP). If the FDPs exceed in a normal value, it represents that cancer in situ has become an invasive cancer. DR-70 can detect cancer cells smaller than $10^6$ cells and is currently a sensitive chemical examination. However, the foregoing analysis may be infected by histoplasma capsulatum, pneumonia, acute infection, autoimmune disease, external trauma (trauma days smaller than thirty days) and interfered with physiological states of hemolysis and pregnancy. Therefore, developing a non-invasive, high sensitivity, high specialty, real-time and inexpensive inspection tools is very important issue.

In addition, after studying patents and master/doctor thesis in Taiwan's universities, the research that relates to biosensor chips in these universities, such as National Taiwan University, National Cheng Kung University, National Tsing Hua University, National Chiao Tung University, National Yang-Ming University, and National Central University has great outcome. Regardless of microelectrospray nozzle chips, cell counting chips and DNA replication chips suitable for detecting protection samples, it has rich research results. However, the biosensor chips developed by Taiwans's academic units do not take microwave filters as a basic structure yet and do not operate a nanometer structure having high frequency electromagnetic wave (larger than 10 GHz) as a tool for detecting and eliminating cancer cells. Therefore, the radio frequency biosensor chip having nanometer structures has great innovation and creativity.

To overcome the foregoing shortcomings, a biosensor chip capable of providing non-invasion, high sensitivity, high specialty, real-time measurement is necessary to overcome the defects of prior arts.

SUMMARY OF THE INVENTION

In view of the shortcomings of the prior art, the inventor(s) of the present invention based on years of experience in the related industry to conduct extensive researches and experiments, and finally developed a radio frequency biosensor chip as a principle objective. The radio frequency biosensor chip has nanometer structures and detects the existence of cancer cells within animal bodies, high frequency characteristics and deteriorate cancer cells in a non-invasive manner.

To achieve the foregoing objective of the invention, a radio frequency biosensor having nanometer structures is provided and includes an isolated substrate, a ground plane, a filtering circuit, at least one cell detection area, a plurality of nanometer structures and a protection layer. The ground plane is deposited at a rear surface of the isolated substrate through a semiconductor process. The filtering circuit is deposited on the isolated substrate through the semiconductor process and has a first signal input/output port and a second signal input/output port. The cell detection area is arranged in the filtering circuit and has equivalent capacitance effect. The nanometer structure is arranged in the cell detection area. The protection layer is coated on the filtering circuit and defines an opening on the cell detection area, the first signal input/output port and the second signal input/output port.

According to a radio frequency biosensor chip having nanometer structures of the invention, the filtering circuit is a conductor-backed coplanar waveguide line structure.

According to a radio frequency biosensor chip having nanometer structures of the invention, an operating frequency of the filtering circuit is at 10 GHz.

According to a radio frequency biosensor chip having nanometer structures of the invention, a material of the nanometer structure is gold.

According to a radio frequency biosensor chip having nanometer structures of the invention, the nanometer structure is a column or a cone structure.

According to a radio frequency biosensor chip having nanometer structures of the invention, a height of the nanometer structure is between 100 nm and 5000 nm, and its diameter is between 10 nm and 500 nm.

According to a radio frequency biosensor chip having nanometer structures of the invention, an operating frequency of the filtering circuit is between 10 GHZ and 50 GHz.

According to a radio frequency biosensor chip having nanometer structures of the invention, the cell detection area is an interdigitated electrode, a low characteristic impedance transmission line or a ring resonator.

According to a radio frequency biosensor chip having nanometer structures of the invention, a material of the filtering circuit is gold (Au) or silver (Ag).

BRIEF DESCRIPTION OF THE DRAWINGS

FIG. 4a is a schematic diagram of a plurality of nanometer structures;

DETAILED DESCRIPTION OF THE PREFERRED EMBODIMENTS

The foregoing and other technical characteristics of the present invention will become apparent with the detailed description of the preferred embodiments and the illustration of the related drawings.

The invention discloses a new type of radio frequency biosensor chip 100 by taking dual-mode bandpass filter as a base and collocates a semiconductor process to realize circuits, thereby detecting amount and size of human hepatoma cells (HepG2) and performing high frequency biological response analysis, such as equivalent resistance, equivalent inductance, equivalent conductance, equivalent capacitor, dielectric permittivity, loss tangent (tan δ), quality factor Q and characteristic impedance of HepG2, as an initial research and development basis. The cell detection area 130 of the radio frequency biosensor chip 100 has equivalent capacitor effect to achieve a simple design method capable of reducing process cost and enhancing the accuracy and sensitivity during measurement.

Figure 1A:
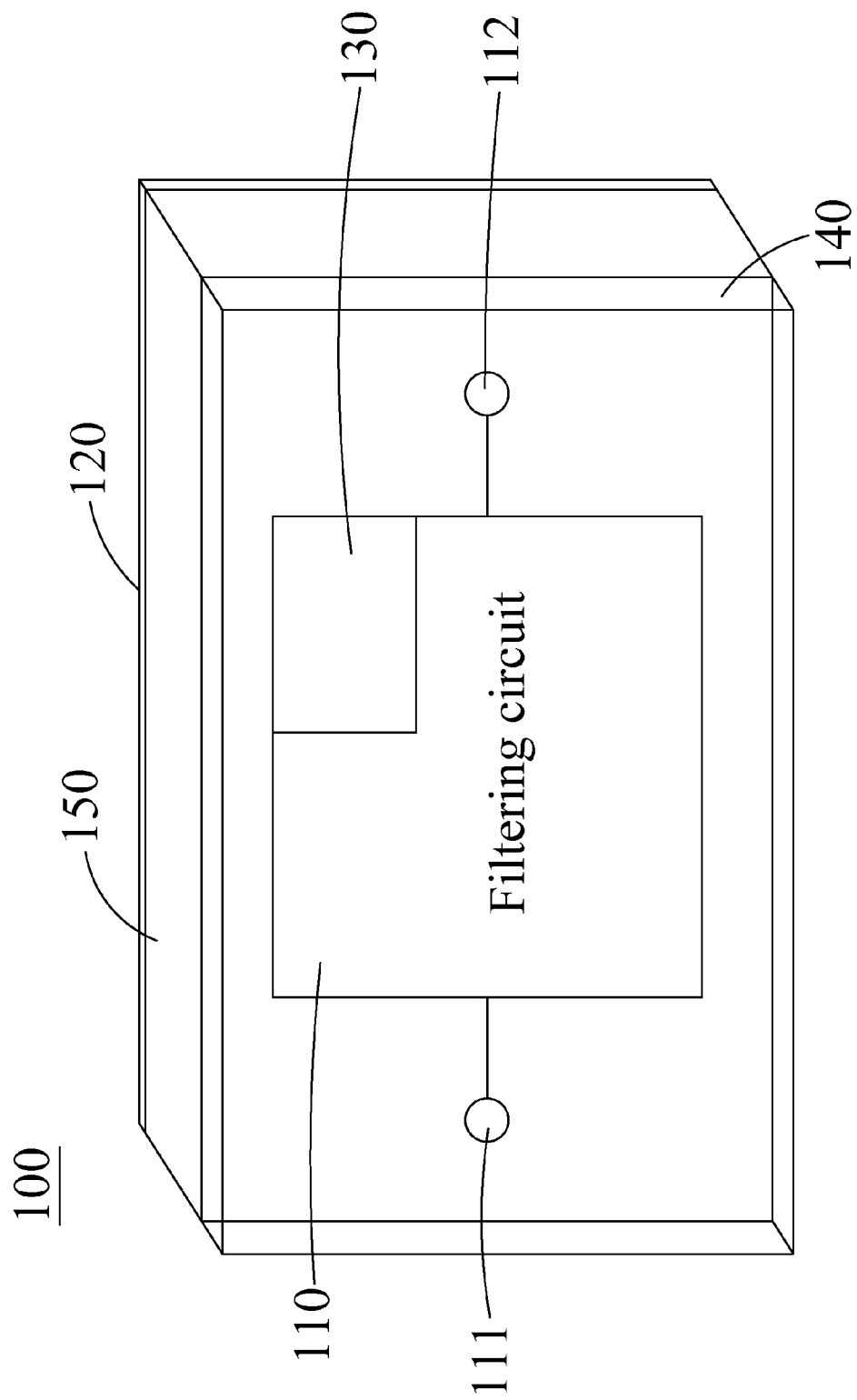
FIG. 1a is a structural diagram of a radio frequency biosensor chip.
Figure 1B:
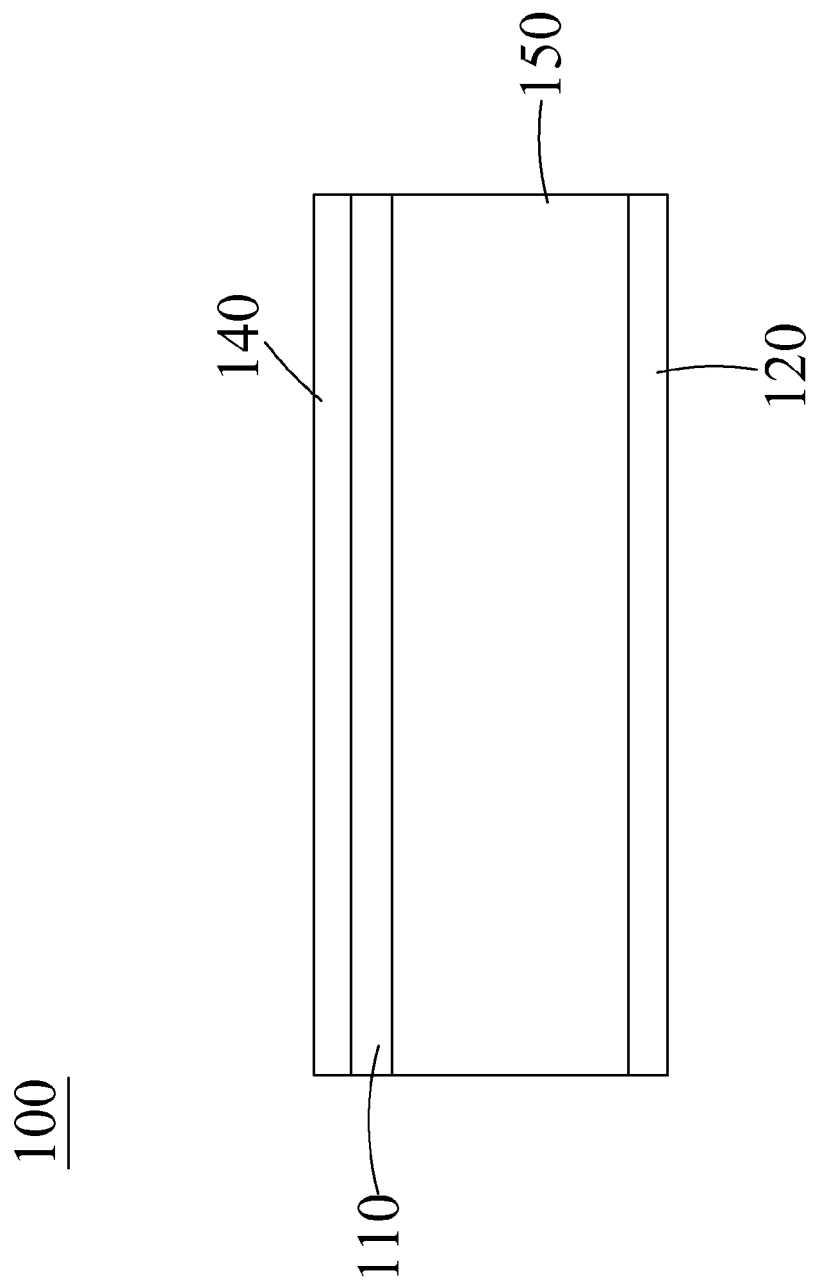
FIG. 1b is a side view of a radio frequency biosensor chip.

With reference to FIG. 1a and FIG. 1b for a structure and side view diagrams of the radio frequency biosensor chip 100 is depicted. The radio frequency sensor chip 100 comprises an isolated substrate 150, a ground plane 120, a filtering circuit 110, at least one cell detection area 130 and a protection layer 140. The ground plane 120 is deposited at a rear surface of the isolated substrate 150 through a semiconductor process. The filtering circuit 110 is deposited on the isolated substrate 150 through a semiconductor process and has a first signal input/output, port 111 and a second signal input/output port 112. The cell detection area 130 is arranged in the filtering circuit 110 and has an equivalent capacitor effect. The protection layer 140 is coated on the filtering circuit 110, and an opening is defined on the cell detection area 130, the first signal input/output port 111 and the second signal input/output port. 112, wherein the filtering circuit. 110 is a conductor-backed coplanar waveguide line structure. The isolated substrate 150 is a glass substrate. The material of the ground plane 120 is gold (Ag) or silver (Ag). The material of the filtering circuit 110 is gold (Ag) or silver (Ag). The filtering circuit 110 includes an interdigitated electrode, a low characteristic impedance transmission line or a ring resonator. According to a preferred embodiment of the invention, the materials of the filtering circuit 110 and the ground plane 120 are Au (2 μm)/Ni(20 nm). The operating frequency of the filtering circuit 110 is at 10 GHz, and the material of the protection layer 140 is a SUS photo resistor.

Figure 2A:
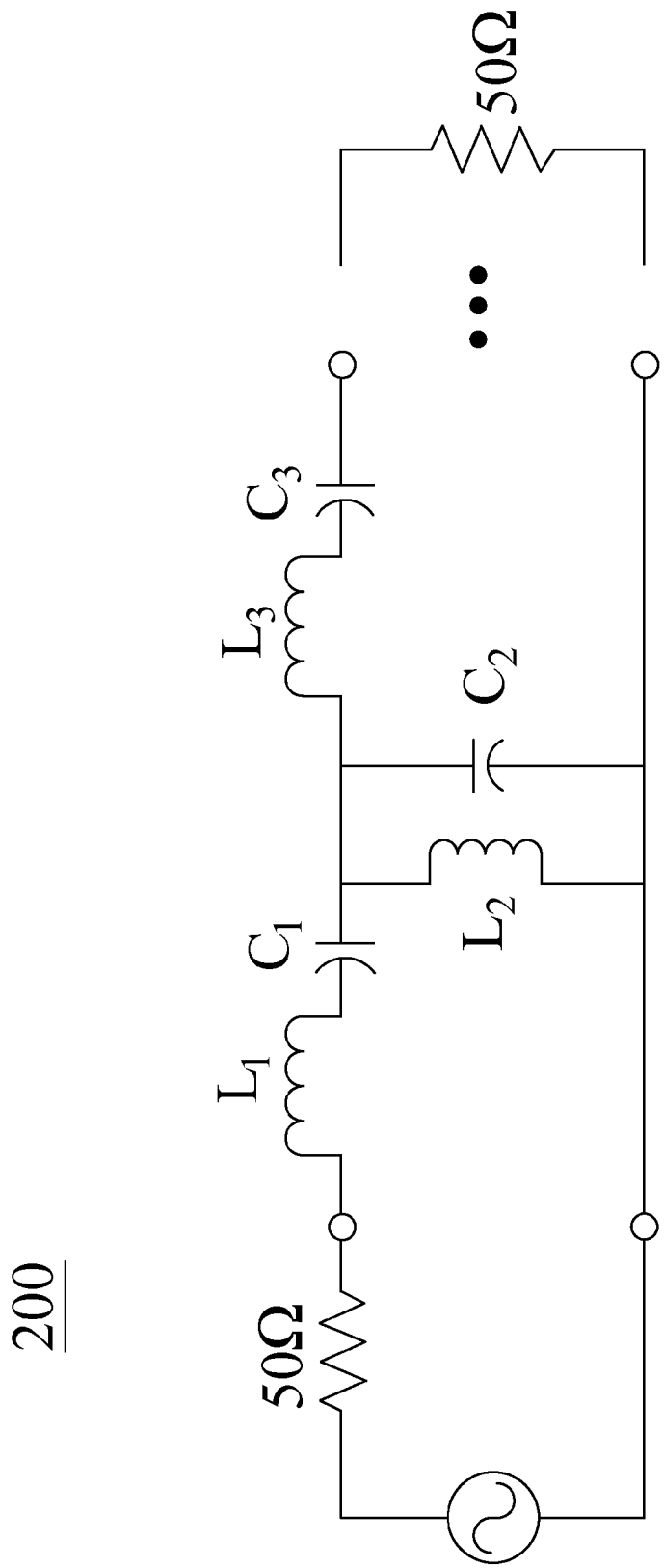
FIG. 2a is a lumped-element equivalent circuit diagram of a bandpass filter.
Figure 2B:
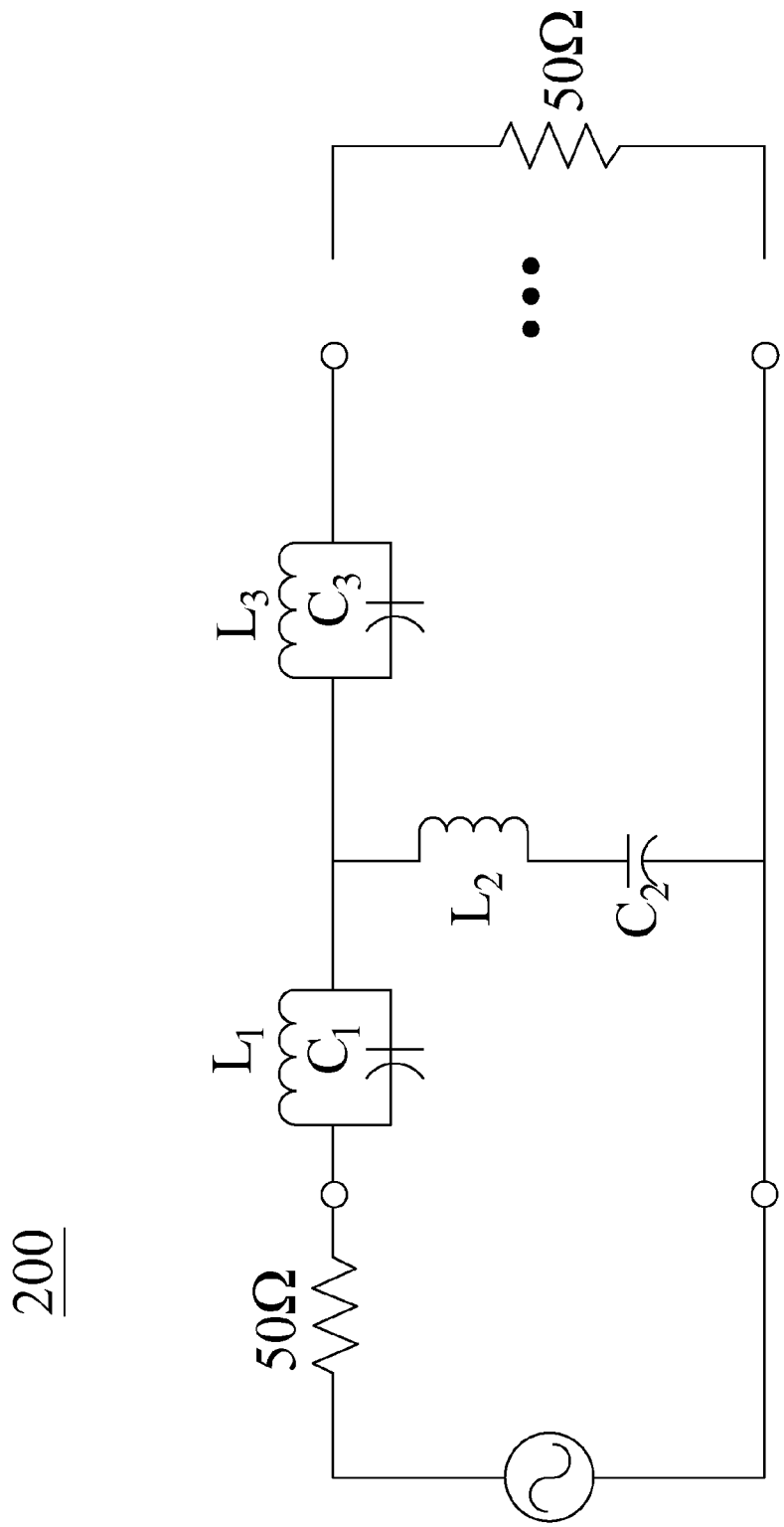
FIG. 2b is a lumped-element equivalent circuit diagram of a band rejection filter.
Figure 3A:
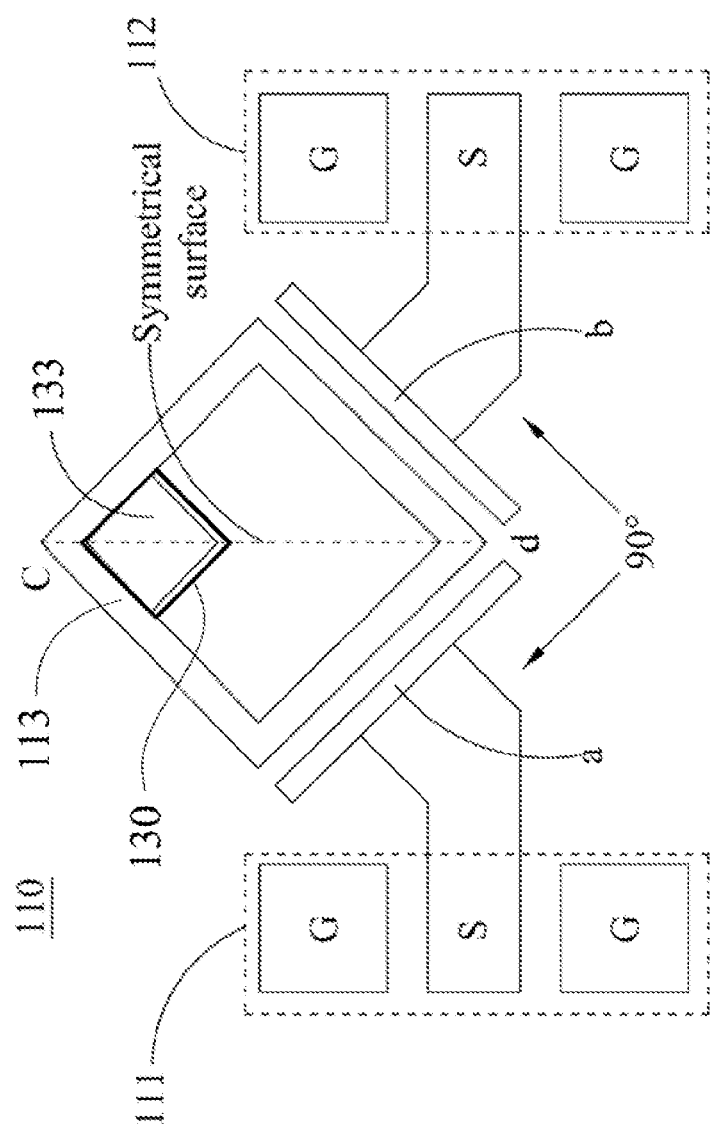
FIG. 3a is a schematic diagram of the radio frequency biosensor chip according to a preferred embodiment of the invention.

With reference to FIG. 2a and FIG. 2b for lumped element type equivalent circuits of a bandpass filter 200 and a band rejection filter 300 are depicted, wherein $L_1$, $L_2$ and $L_3$ are inductors, and $C_1$, $C_2$ and $C_3$ are capacitors and their input/output ends are represented with 50Ω impedance. In a first-order and plural-order filtering circuit 110, the circuit composed of the interdigitated electrode, the low character impedance transmission line or the ring resonator have the equivalent capacitors ($C_1$, $C_2$ and $C_3$). Cells can be placed in the equivalent capacitors that are taken as the cell detection area 130. With reference to FIG. 3a for a radio frequency biosensor chip 100 according to a preferred embodiment is depicted. The radio frequency biosensor chip 100 takes a dual-mode filter as a base. The length of the dual-mode filter is a full guided wavelength ($\lambda g$). A ninety-degree electrical length (a distance from a to b) is between an input end and an output end to have a perturbed structure 133 (which is in the cell detection area 130 and has equivalent capacitors). 135-degree electrical length is between the input/output ends and a perturbed point (i.e., a distance of a to c and b to c). Under a condition of no perturbed structure, the resonant frequency at the input end is activated, its output end may not generate resonance. However, two perpendicular modes generated by the ring resonator 113 and the perturbed structure 133 would reach coupling. The radio frequency biosensor chip 100 takes the conductor-backed coplanar waveguide line as a basis to have an advantage of conveniently designing the resonators and a semiconductor high frequency probe measurement with respect to ground-signal-ground (G-S-G) 111, 112. A common dual-mode filter must have the following conditions:

Ninety-degree electrical length must be separated from the input end to the output end.

A perturbed structure 133 (which is in the cell detection area 130 and has equivalent capacitors) is disposed adjacent to an inner edge of the ring resonator 113 to allow the advancing of electromagnetic wave to have discontinuous phenomenon, thereby activating resonant frequency and generating bandpass.

The circuit structure must be symmetrical.

Figure 3B:
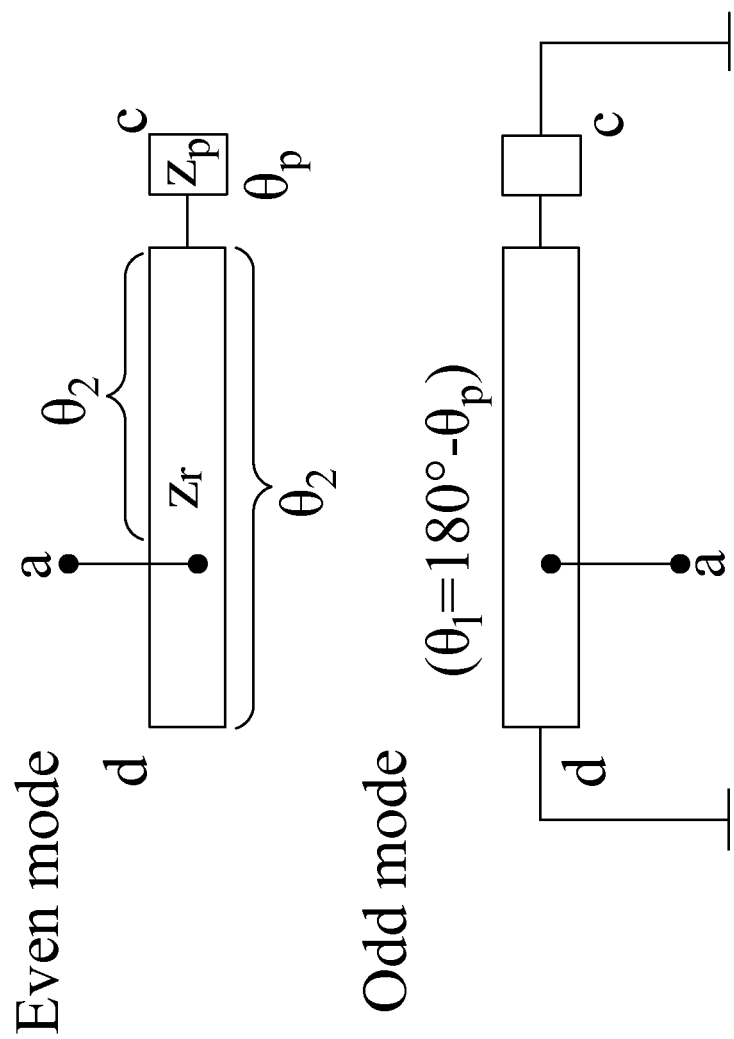
FIG. 3b is an equivalent circuit diagram of the radio frequency biosensor chip.

With reference to FIG. 3b for the equivalent circuit of the radio frequency biosensor chip 100 is depicted. The dual-mode filter is an even mode and odd mode equivalent circuit. Zr is a characteristic impedance of the ring resonator 113, and Zp is a characteristic impedance (since the characteristic impedance is lower, it can be an equivalent capacitor) of the perturbed structure 133, and Kz (Kz=Zp/Zr) is defined as ratio of two impedances. When the ring resonator 113 is not attached with the perturbed structure 133, its electrical length is equivalent to a half-wavelength (a resonant frequency fr). The electrical length of the perturbed structure 133 is 2θp. A position from d point to c point (the perturbed structure 133) is θ.sub. 1. A position from a point (or b point) to c point (the perturbed structure Zp) is θ.sub.2 (θ.sub.2=θ.sub.1-45 degrees). The resonant frequency f.sub.0e of the even mode and the resonant frequency f.sub.0d of the odd mode would satisfy:

f.sub.0d=f.sub.0d/fr,f'.sub.0d is the resonant frequency of the odd mode after normalization. By regulating the electrical length 2θp of the perturbed structure, the formation of passband can be immediately decided to form the frequency response for a classical dual-mode filter. The dual-mode filter has advantages of simple in design, small size and high passband attenuation to be suitable for a basic structure of the radio frequency biosensor chip.

Figure 4B:
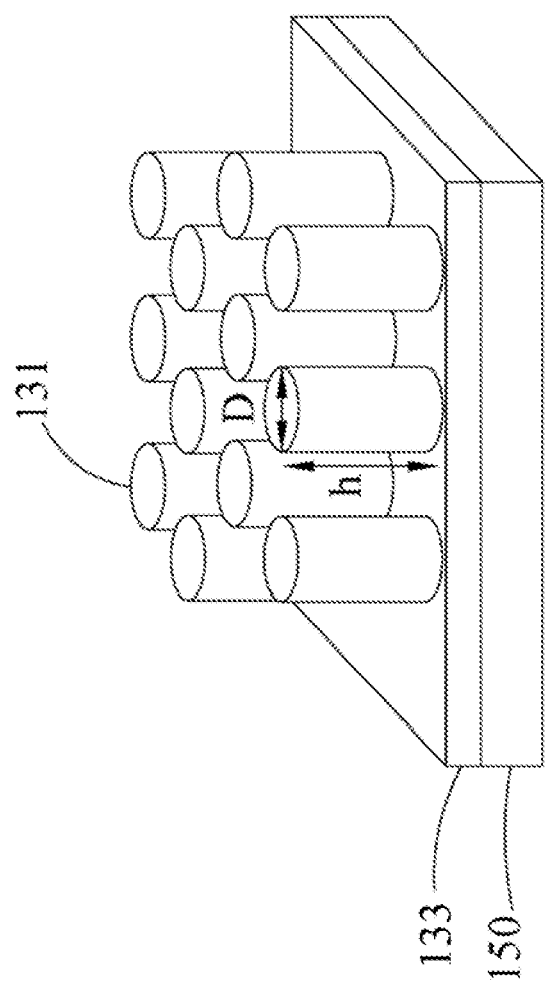
FIG. 4b is a side view of a plurality of nanometer structures.

With reference to FIGS. 4a-4b for a plurality of nanometer structures 131 are depicted. The nanometer structure 131 is a column or cone structure. In response to a preferred embodiment of the invention, the nanometer structure 131 is a column. Its material is gold, and its height (h) is between 100 nm and 5000 nm, and its diameter (D) is between 10 nm and 500 nm. In a process, the substrate 150 is directly delivered to a level furnace tube growing a silicon oxide (SiO.sub.2) layer in which a thickness is between 100 nm and 500 nm after rinsing with a standard RCA sequence, thereby preventing the substrate 150 from generating leakage current and conduction during measurement. Next, a test strip is rinsed through alcoholic solution. After drying with nitrogen gas, the test strip is placed into a vapor deposition system to perform vacuum pumping for 3 to 4 hours until a vacuum value reaches below 5×10.sup.-6 torr. A gold film then is deposited by vapor deposition. Its deposition condition is that: a thickness between 100 nm and 5000 nm; a temperature of the substrate 150 is below 200 degree Celsius through control. The highest evaporation rate is 1 angstrom/second. The test strip that is completed with film plating then undergoes a thermal oxidation process at different conditions via a vacuum annealing furnace tube, thereby growing gold nano-columns in which a temperature is about 400° C., 500° C. and 600° C.; a temperature retention time is about 1, 3 and 5 hours; and oxygen flow is about 10, 20 and 30 seen. The Scanning Electron Microscope (SEM) is utilized to observe the material and electric properties of gold-nano columns, and an optimum condition of growing Titania nan-columns is obtained to provide a sample for subsequent analysis and surface plasma modification.

Figure 5:
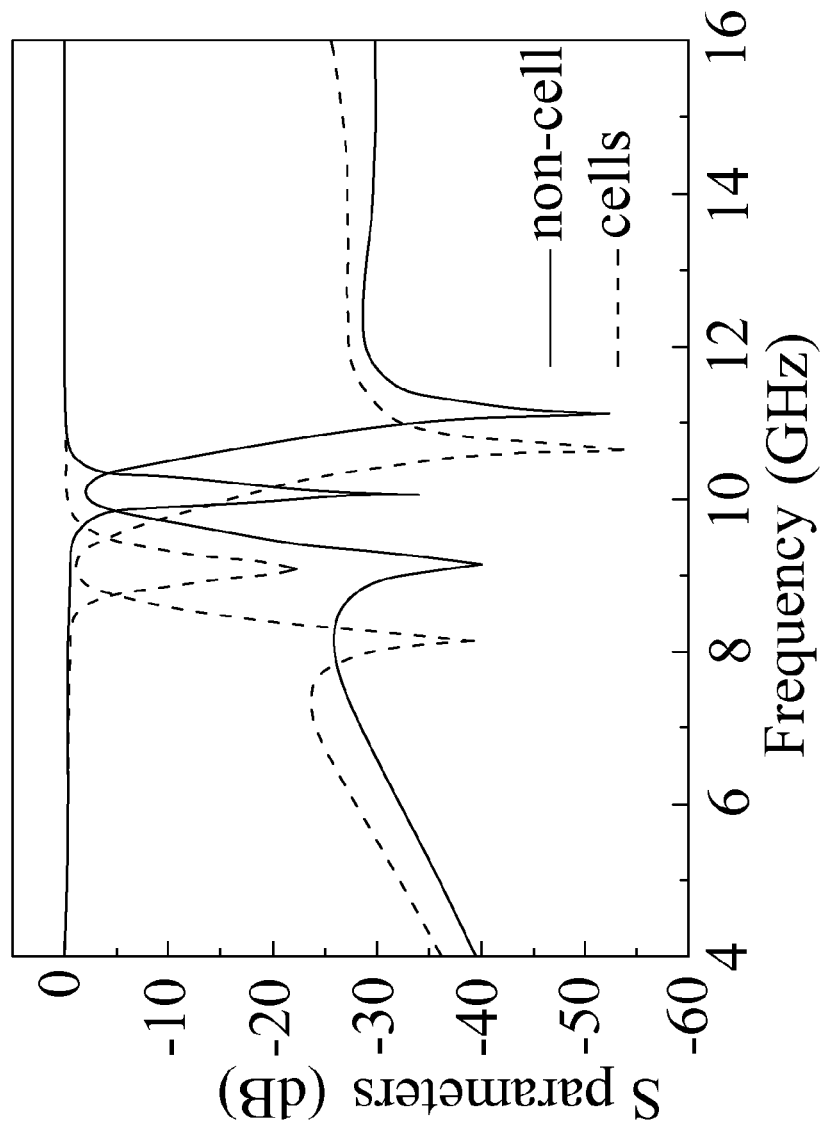
FIG. 5 is a schematic diagram of a frequency response of the radio frequency biosensor chip.

In the measurement, its instrument needs to use a vector network analyzer (VNA) HP 8510C of high frequency probe stations 111, 112 containing G-S-G, wherein its measurement scope is between 0.045 and 50 GHz. With reference to FIG. 5 for a frequency response of the radio frequency biosensor chip 100 is depicted. For example, cell amount in a culturing process can be obtained by a conventional cell counting method. The cells then are placed in the detection area of the radio frequency biosensor chip to observe the frequency response (including the variation of the center frequency, bandwidth, insertion loss and return loss under loaded cells and unloaded cells), thereby analyzing sizes, quantity and high frequency dielectric properties (e.g. the equivalent resistance (R) of hepatoma cells), inductance (L), conductance (G) and capacitance (C), dielectric coefficient and loss tangent) of cells.

While using the network analyzer, error calibration must be carried out, including random errors, systematic errors, and drift errors. The random errors are mainly from noise of the system and the reliability of components in the instrument; these errors are unable to be eliminated by calibration. The systematic errors are mainly from the circuit design of the measurement instrument and can be eliminated by calibration. The drift errors are mainly that the performance of the system is different at different time and different conditions such as the change of ambient temperatures. This kind of errors can be eliminated by repeated calibration. The systematic error is reduced to below −50 dB after calibration, thereby decreasing the mistake during the measurement. After detecting the chip, the chip is immersed into phosphate buffer saline (PBS). An ultrasonic oscillator is utilized for 30 minutes to remove cells remained on the chip. After completing oscillation, the radio frequency biosensor chip 100 can be repeatedly used. In addition, the nanometer structure 131 can effectively pierce through cancer cells to transmit electromagnetic wave, in which the frequency is between 10 and 50 GHz, around the cancer cells to achieve the purpose of deteriorating the cancer cells.

Hepatoma cells are taken as an example. When the nanometer structure 131 pierces through cells, the frequency response of the filter passband is shifted. According to the displacement quantity, the equivalent RLGC value, dielectric coefficient and loss tangent of cells can be further calculated. Four sets of Scattering parameters can be obtained from the displacement quantity, the parameters are S.sub.11, S.sub.12, S.sub.21 and S.sub.22 respectively, and these parameters are put into formula (3) to obtain a propagation constant γ(f):

$$e^{-\gamma l} = \left[\frac{1 - S_{11}^2 + S_{21}^2}{2S_{21}} \pm k\right]^{-1} \tag{3}$$

wherein $$k = \left[\frac{(S_{11}^2 - S_{21}^2 + 1)^2 - (2S_{11})^2}{(2S_{21})^2}\right]^{1/2},$$

and plural propagation constants can be rewritten into:

$$\gamma(f) = \alpha_r(f) + j\beta(f) \tag{4}$$

wherein $\alpha t(f)$ is an attenuation constant, and $\beta(f)$ is a phase constant, and both constants are:

$$\alpha_t(f) = 8.686 \cdot \left[-\frac{1}{L}\text{Re}\left\{\ln\left[\frac{1 - S_{11}^2 + S_{21}^2}{2S_{21}} \pm k\right]^{-1}\right\}\right] = \alpha_c + \alpha_d \text{(dB/mm)} \tag{5}$$

$$\beta(f) = -\frac{1}{L}\text{Im}\left\{\ln\left[\frac{1 - S_{11}^2 + S_{21}^2}{2S_{21}} \pm k\right]^{-1}\right\} = \frac{2\pi \cdot f\sqrt{\varepsilon_{\text{eff}}(f)}}{c} \text{(rad/mm)} \tag{6}$$

with formula (6), an effective dielectric coefficient ∈eff(f) can be obtained. The characteristic impedance Z.sub.0 is:

$$Z_0 = \frac{\eta_0}{\sqrt{\varepsilon_{\mathit{eff}}}} \left\{ \frac{w}{h} + 0.883 + \frac{\varepsilon_{\mathit{eff}}+1}{\pi\varepsilon_{\mathit{eff}}}\left[\ln\left(\frac{w}{2h}+0.94\right)+1.451\right] + 0.165 \cdot \frac{\varepsilon_{\mathit{eff}}-1}{\varepsilon_{\mathit{eff}}^2} \right\}^{-1} \quad (7)$$

According to the following formula, the equivalent resistance (R), the inductance (L), the conductance (G) and capacitance (C) of cells can be obtained:

$$\gamma(f) \times Z_0(f) = R + j\omega L \quad (8)$$

$$\gamma(f)/Z_0(f) = G + j\omega C \quad (9)$$

With the following formula, the dielectric coefficient of the cells can be obtained:

$$\in_{\mathit{eff}} = (1-q) + q\in_r \quad (10)$$

wherein q is a structure factor of the microstrip, and its loss tangent can be represented as the following:

$$\tan\delta = \frac{\alpha_d \sqrt{\varepsilon_{\mathit{eff}}} \, (\varepsilon_r - 1)\lambda_0}{27.3\varepsilon_r(\varepsilon_{\mathit{eff}}-1)} \quad (11)$$

The invention improves over the prior art and complies with patent application requirements, and thus is duly filed for patent application. While the invention has been described by device of specific embodiments, numerous modifications and variations could be made thereto by those generally skilled in the art without departing from the scope and spirit of the invention set forth in the claims.

What is claimed is:

1. A radio frequency biosensor chip having nanometer structures comprising:
   an isolated substrate;
   a ground plane deposited at a rear surface of the isolated substrate through a semiconductor process;
   a ring resonator deposited on the isolated substrate through the semiconductor process, wherein the ring resonator is operated at an operating frequency of 10 GHz, wherein a physical length of the ring resonator itself is a full guided wavelength;
   a first signal input/output port and a second signal input/output port connected to the ring resonator, wherein a distance between the first signal input/output port and the second signal input/output port is ninety-degree electrical length when the ring resonator is operated at an operating frequency of 10 GHz;
   a perturbed structure having an electrical length and being disposed adjacent to an inner edge of the ring resonator to form at least one cell detection area for receiving a test cell and allow electromagnetic wave advancing discontinuously for activating a resonant frequency and generating a passband, wherein a circuit structure, which is a combination of the ring resonator and the perturbed structure, is symmetrical, wherein a distance between the perturbed structure and the first signal input/output port and a distance between the perturbed structure and the second signal input/output port are 135-degree electrical length, wherein the perturbed structure has an equivalent capacitance which is taken as the cell detection area, wherein the center frequency of the passband is determined by the electrical length of the perturbed structure;
   a plurality of nanometer structures formed on the perturbed structure, wherein each of the nanometer structures is a column or a cone structure with a height between 100 nm and 5000 nm and a diameter between 10 nm and 500 nm, wherein a frequency response of the circuit structure is formed when a measurement scope of the radio frequency biosensor chip is between 0.045 and 50 GHz by using the first signal input/output port and the second signal input/output port, wherein when the nanometer structures pierce through the test cell, the equivalent capacitance of the perturbed structure is changed, and the electromagnetic wave with a frequency of 10 GHz is transmitted from the ring resonator into the test cell via the nanometer structures for deteriorating the test cell; and
   a protection layer coated on the ring resonator and the isolated substrate, the protection layer defining openings on the cell detection area, the first signal input/output port and the second signal input/output port.

2. The radio frequency biosensor chip having nanometer structures as recited in claim 1, wherein the biosensor chip is a conductor-backed coplanar waveguide line structure.

3. The radio frequency biosensor chip having nanometer structures as recited in claim 1, wherein a material of the nanometer structures is gold.

4. The radio frequency biosensor chip having nanometer structures as recited in claim 1, wherein the isolated substrate is a glass substrate.

5. The radio frequency biosensor chip having nanometer structures as recited in claim 1, wherein the cell detection area is a low characteristic impedance transmission line.

6. The radio frequency biosensor chip having nanometer structures as recited in claim 1, wherein the filtering circuit is a multi-layer structure of an Au layer with thickness of 2 μm and a Ni layer with thickness of 20 nm.

7. The radio frequency biosensor chip having nanometer structures as recited in claim 1, wherein the ground plane is a multi-layer structure of an Au layer with thickness of 2 μm and a Ni layer with thickness of 20 nm.

* * * * *